United States Patent
Burtscher et al.

(10) Patent No.: US 7,335,250 B2
(45) Date of Patent: Feb. 26, 2008

(54) DENTAL COMPOSITES BASED ON X-RAY-OPAQUE MIXED OXIDES PREPARED BY FLAME SPRAYING

(75) Inventors: Peter Burtscher, Rankweil (AT); Lutz Mädler, Zürich (CH); Norbert Moszner, Eschen (LI); Sotiris E. Pratsinis, Zürich (CH); Volker M. Rheinberger, Liechtenstein (DE)

(73) Assignee: Ivoclar Vivadent AG, Liechtenstein (DE)

( * ) Notice: Subject to any disclaimer, the term of this patent is extended or adjusted under 35 U.S.C. 154(b) by 201 days.

(21) Appl. No.: 10/951,994

(22) Filed: Sep. 29, 2004

(65) Prior Publication Data

US 2005/0176843 A1    Aug. 11, 2005

(30) Foreign Application Priority Data

Feb. 6, 2004 (DE) .................. 10 2004 006 564
Apr. 7, 2004 (DE) .................. 10 2004 017 125

(51) Int. Cl.
*A61K 6/00* (2006.01)

(52) U.S. Cl. ................. 106/35; 523/105; 523/117; 433/226; 433/228.1; 433/222.1

(58) Field of Classification Search ............. 106/35; 523/105, 117; 433/226, 228.1, 222.1; 423/293; 65/17.4; 264/5, 11
See application file for complete search history.

(56) References Cited

U.S. PATENT DOCUMENTS

| | | | |
|---|---|---|---|
| 4,301,029 A | 11/1981 | Caunt et al. | |
| 6,569,397 B1 * | 5/2003 | Yadav et al. | 423/345 |
| 6,656,588 B1 * | 12/2003 | Laine et al. | 428/402 |
| 7,090,721 B2 * | 8/2006 | Craig et al. | 106/35 |
| 2002/0035950 A1 * | 3/2002 | Mangold et al. | 106/482 |
| 2002/0095014 A1 | 7/2002 | Fottinger et al. | |
| 2003/0086855 A1 * | 5/2003 | Konya et al. | 423/335 |

FOREIGN PATENT DOCUMENTS

| | | |
|---|---|---|
| EP | 004 645 | 10/1979 |
| EP | 014 523 | 8/1980 |
| EP | 032 307 | 7/1981 |
| EP | 089 691 | 9/1983 |
| EP | 120 503 | 10/1984 |
| EP | 241 947 | 10/1987 |
| EP | 416 815 | 3/1991 |
| EP | 420 436 | 4/1991 |
| EP | 439 964 | 8/1991 |
| EP | 494 084 | 7/1992 |
| EP | 594 915 | 5/1994 |
| EP | 595 574 | 5/1994 |
| EP | 744 416 | 11/1996 |
| WO | 98/22486 | 5/1998 |
| WO | 98/27124 | 6/1998 |

OTHER PUBLICATIONS

Brunauer et al., Journal of American Chem. Soc. 60 (1939), pp. 309-319.

* cited by examiner

*Primary Examiner*—C. Melissa Koslow
(74) *Attorney, Agent, or Firm*—Novak Druce & Quigg, LLP

(57) ABSTRACT

The present invention relates to dental composites comprising at least one nanoparticulate mixed oxide (a) of $SiO_2$ with X-ray-opaque metal oxides of one or more elements selected from the group consisting of Y, La, Ce, Pr, Nd, Sm, Eu, Gd, Tb, Dy, Ho, Er, Tm, Yb, Lu which has been prepared by flame spraying.

17 Claims, 2 Drawing Sheets

DENTAL COMPOSITES BASED ON X-RAY-OPAQUE MIXED OXIDES PREPARED BY FLAME SPRAYING

Figure 1:
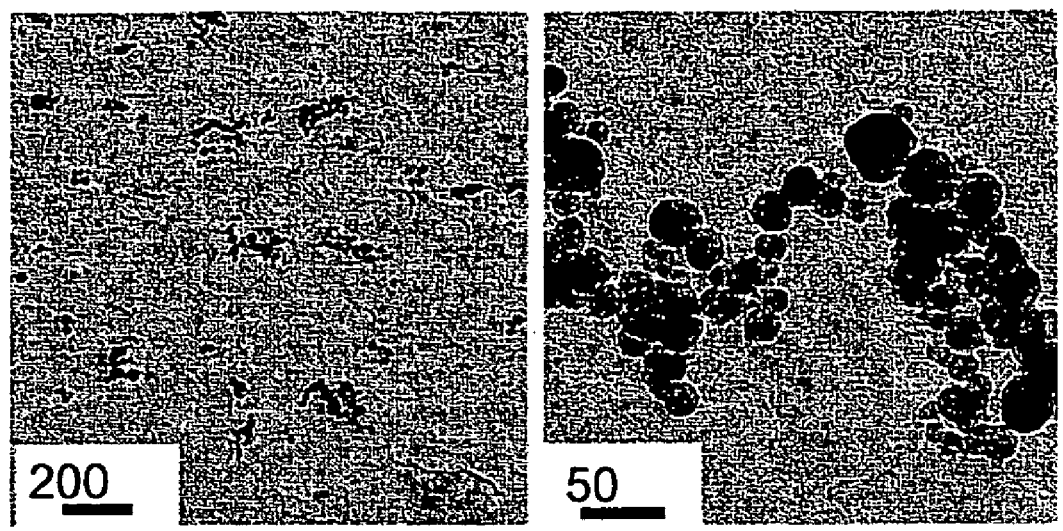

The present invention relates to the use of at least one nanoparticulate mixed oxide (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu which has been prepared by flame spraying as X-ray-opaque filler in dental composites, to the resulting dental composites and to their production and use.

DEFINITIONS OF TERMS

Amorphous solids are homogeneous, noncrystalline solids in which the molecular building blocks are bound to one another by more or less pronounced short-range ordering similar to the situation in a crystal but do not have the long-range order, i.e. regular repetition of a unit cell, characteristic of crystals. In contrast to crystalline substances, such amorphous substances are fully isotropic. For the purposes of the present invention, amorphous substances are ones which have a crystallinity index of less than 0.1, preferably less than 0.05, in each case determined by X-ray diffraction (0=amorphous; 1.0=crystalline). This means that, on the basis of X-ray or electron diffraction, amorphous substances are ones in which no resolvable structures are visible in the diffraction pattern. Further details may be found in relevant physics or chemistry textbooks.

For the purposes of the present invention, a homogeneous element distribution is a distribution in which the elements are uniformly mixed with one another, i.e. there is an essentially random distribution of the elements without regions in which an individual element is present in a higher concentration. Accordingly, the distribution of the elements in the corresponding particles is uniform when it does not change in different regions of the particles, i.e. there are no concentration gradients of the elements within the respective particles.

For the purposes of the present invention, a very low organic content means that less than 0.5% by mass, preferably less than 0.1% by mass, of oxidizable carbon, in particular no organic carbon, i.e. amounts below the detection limit, are present.

Variable in the context of the X-ray opacity of the substances according to the invention means that the X-ray opacity can be adjusted within certain limits in a conventional way by a person skilled in the art via the parameters in the preparation of the mixed oxides, i.e. by means of starting materials, concentration, temperature, etc. The X-ray opacity of the composites based on the mixed oxides according to the invention can be set in the range from 50% Al to 800% Al, in particular from 100% Al to 400% Al.

Variable in the context of the index of refraction of the mixed oxides according to the invention means that the index of refraction can be adjusted within certain limits in a conventional way by a person skilled in the art via the parameters in the preparation of the mixed oxides, i.e. by means of starting materials, concentration, temperature, etc. The index of refraction of the mixed oxides according to the invention can be set in the range from 1.46 to 1.70, in particular from 1.48 to 1.60.

For the purposes of the present invention, spherical means that the primary particles concerned are spheroidal and display no preferential direction or edges in the transmission electron micrograph (TEM), comparable to the case of ideal spheres.

For the purposes of the present invention, the expression (meth)acryl . . . encompasses both methacryl . . . and acryl.

PRIOR ART

In dentistry, composites are used mainly as direct filling material for cavities, as fixing cement or as material for inlays or facing materials. They are mostly made up of an organic monomer or polymer matrix and fillers embedded therein. The organic resin matrix of present-day dental filling composites is based largely on dimethacrylates such as bis-GMA (an addition product of methacrylic acid and bisphenol A diglycidyl ether), UDMA (an addition product of 2-hydroxyethyl methacrylate and 2,2,4-hexamethylene diisocyanate) or TEGDMA (triethylene glycol dimethacrylate). The fillers are usually siliceous in nature, with these being surface-treated with a polymerizable silane to obtain an optimum bond between resin matrix and the filler particles. The fillers ensure, in particular, satisfactory mechanical properties such as high compressive and flexural strength or hardness, a low coefficient of thermal expansion and a reduction in heat evolution and volume contraction on curing, and also serve to adjust the optical properties and the X-ray opacity (E. C. Combe, F. J. T. Burke, W. H. Douglas, Dental Biomaterials, Kluwer Academic Publ., Boston 1999, p. 237). X-ray opacity is achieved mainly by incorporation of elements having a high atomic number (e.g. Ba or Sr) in the fillers. In the case of glass fillers, a large number of elements (Si, Al, B, Ba, Sr or La) can be used in various proportions and the index of refraction can therefore be varied in a wide range (1.46 to 1.55), but the nanofillers used hitherto are based essentially on silicon dioxide ($SiO_2$), as a result of which the index of refraction is restricted to a range from 1.42 to 1.49. Optimum matching of the indices of refraction of filler and polymerized matrix is a prerequisite for a high transparency of the composite and is thus a fundamental requirement for aesthetic restorations.

Monomers based on dimethacrylates enable the index of refraction of the polymerized matrix to be set within a wide range (1.45 to 1.55); the most reactive monomers, e.g. bis-GMA, are aromatic in nature and have an index of refraction of about 1.55.

Monomers having an index of refraction of from 1.52 to 1.55 are preferred according to the invention.

The X-ray opacity of silicon oxide is very low, so that a composite based on this filler has only a low X-ray opacity, which makes dental diagnostics more difficult. X-ray-opaque fillers such as ytterbium fluoride or X-ray-opaque glasses have a significantly higher index of refraction (1.51 to 1.55) than $SiO_2$. However, the simultaneous use of fillers having different indices of refraction reduces the transparency and thus the aesthetics. For this reason, composites comprising purely nanofillers have only a low X-ray opacity at acceptable optical properties. In contrast, X-ray opaque composites based on nanofillers have a transparency which is too low. X-ray-opaque metal oxide fillers suitable for dental composites are known from the following prior art:

Amorphous, spherical inorganic compounds which have a particle size of from 0.1 to 1.0 μm and are based on $SiO_2$ and at least one oxide of the elements of groups I to IV and are prepared via a wet chemical synthesis are described in DE 32 47 800. Dental composites based on these are disclosed in DE 40 29 230.

DE 195 08 586 describes fillers which are obtained by coating an $SiO_2$ core with an oxide of an element of groups I to IV by a sol-gel process. Such fillers are also mentioned in DE 197 41 286.

Polymerizable metal oxide particles which have a core-shell structure are disclosed in DE 198 46 660. Such fillers can be obtained by surface modification of, for example, commercial SiO$_2$ particles with metal alkoxides.

Oxide particles which are suitable as fillers for dental materials and comprise a core of any oxide of a metal or a metalloidoxide of the Periodic Table, any doping component distributed in the core and a shell surrounding the core are described in EP 1 243 552. These particles are prepared by firstly introducing the dopant into the core in a pyrogenic process via an aerosol and subsequently surrounding the core by a shell.

EP 1 236 459 describes light-curing dental composites which have excellent handling properties and fracture toughnesses and comprise a filler made up of a mixture of size-matched particles of irregular shape (0.1 to 1.0 μm), spherical particles (0.1 to 5.0 μm) and very small particles (less than 0.1 μm). As materials for the filler particles, mention is made of, for example, SiO$_2$—ZrO$_2$ or SiO$_2$—TiO$_2$.

Nanoparticulate metal oxide or mixed oxide fillers are of particular interest for use in dental materials, e.g. as filling composites, since, firstly, they make it possible to combine various properties, e.g. high flexural strength, low abrasiveness and optimum X-ray opacity, and, secondly, make it possible to produce transparent or translucent materials, i.e. materials having tooth-like aesthetic properties, as a result of their low particle size (smaller than 100 nm) (cf. "Nanotechnology for Dental Composites" N. Moszner, S. Klapdohr, Intern. J. Nanotechn., 1 (2004) 130-156). Such nanoparticulate metal oxide fillers can be prepared, for example, by a wet chemical route by means of hydrolytic condensation (sol-gel process) of individual metal alkoxides or mixtures thereof or by means of flame pyrolysis of suitable precursor compounds such as metal alkoxides, salts or halides. The physical and chemical properties of the nanoparticles depend, inter alia, on their chemical composition and morphology, their particle size or size distribution and the surface modification.

The use of combinations of nanoparticle oxides in which at least one oxide is a nanoparticulate and X-ray-opaque metal oxide component as dental fillers is known from the following prior art:

nanosize, pyrogenic yttrium-zirconium mixed oxide having a specific surface area of from 1 to 800 m$^2$/g is described in DE 101 38 573 as ceramic base material for dental materials.

DE 100 18 405 describes spherical oxide particles which have a particle size of from 5 to 10 000 nm and comprise from 0.1 to 99.9% by weight of an oxide of titanium, aluminum, zirconium, yttrium or silicon and at least one further oxide of the lanthanides, with the particles being able to have a core-shell structure or a homogeneous distribution of the metal oxides.

Dental materials based on nanoparticle fillers comprising SiO$_2$ particles together with, as X-ray-opaque filler, nanoparticulate heavy metal oxides of metals having an atomic number of more than 28 are described in WO 01/30304, WO 01/30305, WO 01/30306, WO 01/30307. Particularly preferred oxides are said to be, for example, La, Zn, Sn, Y, Yb, Ba and Sr oxides or combinations thereof, with the preferred particle size being less than 60 nm. Mixed oxides of SiO$_2$ and Yb$_2$O$_3$ are not mentioned. In addition, it is stated that the heavy metal oxide components described can represent part of the coating of the SiO$_2$ particles. Furthermore, amorphous, nanoparticulate clusters which are preferably obtainable from oxides other than heavy metal oxides, e.g. SiO$_2$ or As$_2$O$_3$, and oxides of heavy metals, e.g. La, Zn, Sn, Y, Yb, Ba or Sr, are also claimed. Here, the term cluster refers to the way in which the particles are joined, with the heavy metal oxides in the clusters being present as individual particles, as a coating on the particles comprising oxides other than heavy metal oxides or as a region in the particles comprising oxides other than heavy metal oxides. In addition, the heavy metal oxide can be present in the particles comprising oxides other than heavy metal oxides as a solid solution (e.g. as a continuous glass) or as a precipitate in a second phase. Furthermore, it is stated that the clusters display essentially no crystallinity, i.e. the fillers claimed preferably have a crystallinity index below 0.1 (0=amorphous; 1.0=crystalline). In the examples, SiO$_2$ and ZrO$_2$ are used as metal oxides and the clusters are prepared by, for example, modifying commercial SiO$_2$ particles with zirconyl acetate by a sol-gel process.

Ta$_2$O$_5$—SiO$_2$ particles having a diameter of from 50 to 100 nm are claimed in U.S. Pat. No. 6,417,244 B1. Here, the synthesis of the particles starts out from dispersions of monodisperse SiO$_2$ particles (10 to 20 nm) and Ta$_2$O$_5$ particles (1 to 2 nm).

WO 99/17716 describes low-viscosity dental materials comprising nonagglomerated nanoparticles having a size of from 1 to 100 nm, with fillers mentioned being, inter alia, pyrogenic silica, tantalum oxide and niobium oxide and mixtures thereof.

US 2002/0002214 A1 describes cationically polymerizable compositions comprising, as X-ray-opaque fillers, oxides, oxide mixtures or mixed oxides of the elements La, Zn, Ta, Sn, Zr, Y, Yb, Ba, Sr with oxides of the elements Al, B or Si which are obtainable by the sol-gel process or via a melt. No particle size is reported for the fillers.

Fillers based on ormocer mixed oxide particles of the elements Ti, Zr, Y, La, Ta and Al with organosilicon or organotitanium components, which contain organic groups and do not scatter visible light in the range from 360 to 830 nm, are described in GB 2 304 720.

The nanoparticulate fillers which are described in the above-cited prior art and in which SiO$_2$ has been combined with an X-ray-opaque metal oxide contribute, as a result of their two-phase morphology (e.g. core/shell, doping, mixing of oxides) and the associated inhomogeneous element distribution in the solid and also the partially crystalline structure, only unsatisfactorily to transparent properties in the composite. In addition, matching of the index of refraction of the fillers to that of the matrix is possible to only a limited extent. Furthermore, the nanoparticulate, nonspherical fillers usually display an extremely high thickening action which is very difficult to influence.

A further disadvantage of wet chemical processes for preparing mixed oxides is that in the case of incomplete drying (complete drying is extremely difficult) small amounts of residual solvent always remain and these can then, during the subsequent calcination, lead to discoloration of the particles and thus also the dental composite. Such discolored products can generally not be used for aesthetic reasons and thus constitute reject material.

DESCRIPTION OF THE INVENTION

It is an object of the invention to provide dental composites which, compared to the prior art, have a good X-ray opacity at a high transparency and a low intrinsic color caused by the filler, allow variation of the X-ray opacity, of the index of refraction and of the thickening action of the filler and are suitable for producing cements, facing materials and especially filling composites for dental purposes.

According to the invention, this object is achieved by dental composites comprising at least one nanoparticulate mixed oxide (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu, where the mixed oxides are prepared by flame spraying, and have at least one, in particular all of: (a) an amorphous structure, (b) a homogeneous element distribution, (c) a very low organic content, (d) a variable X-ray opacity, (e) a variable index of refraction and (f) a spherical particle shape, and display a reduced thickening action which is reduced due to agglomeration.

The mixed oxides according to the invention have a very homogeneous element distribution which has not been able to be achieved using previous wet chemical methods.

The elimination of a solvent as is necessary in wet chemical processes not only eliminates the above-mentioned disadvantages but also eliminates the need for it to be removed subsequently and avoids agglomerate formation which leads to relatively large secondary particles having a broader particle size distribution and consequently a lower transparency. The preparation of the mixed oxides according to the invention is also, as a result of it being a continuous process, able to be carried out in a more economically favorable and simpler fashion.

Another advantage is that the choice of components in the synthesis by flame spraying enables the index of refraction of the primary particles to be adjusted at an extremely small particle size (less than 50 nm) and a narrow particle size distribution.

Likewise, the particle size of the mixed oxides according to the invention can be adjusted in a targeted manner by means of the process used for preparing them.

In flame spray pyrolysis, the reactor comprises a multifluid nozzle which is surrounded concentrically by an auxiliary flame (L. Mädler, H. K. Kammler, R. Mueller, and S. E. Pratsinis, "Controlled synthesis of nanostructured particles by flame spray pyrolysis", Journal of Aerosol Science, vol. 33, pp. 369-389, 2002; L. Mädler, W. J. Stark, and S. E. Pratsinis, "Flame-made ceria nanoparticles", Journal of Materials Research, vol. 17, pp. 1356-1362, 2002; R. Mueller, L. Mädler, and S. E. Pratsinis, "Nanoparticle synthesis at high production rates by flame spray pyrolysis", Chemical Engineering Science, vol. 58, pp. 1969-1976, 2003). The auxiliary flame serves to ignite the spray and is supplied with a combustible gas mixture (e.g. $CH_4/O_2$, $H_2/O_2$). The multifluid nozzle disperses at least one combustible liquid to give fine droplets which in the ideal case have a size of from 1 µm to 100 µm. In addition, an enveloping stream of air can be provided outside the protective flame. The particles formed in the spray flame are cooled by mixing with ambient air. However, other cooling methods are likewise possible, e.g. injection of liquids having a high enthalpy of vaporization or nozzle quenching (K. Wegner and S. E. Pratsinis, "Nozzle-quenching process for controlled flame synthesis of titania nanoparticles", AIChE Journal, vol. 49, pp. 1667-1675, 2003). The gas-borne particles are then deposited on a suitable filter and cleaned off from this. The liquid which is dispersed comprises both the fuel and the precursors of the metal oxide. As precursors for $SiO_2$, particular preference is given to tetraalkoxysilanes, e.g. trimethylsilane or tetraethylsilane. In the case of the X-ray-opaque metal oxides of elements selected from the group consisting of Y, La, Ta, Ce, Pr, Nd, Sm, Eu, Gd, Tb, Dy, Ho, Er, Tm, Yb and Lu, suitable precursors are corresponding metal salts such as nitrates, halides or carboxylates, e.g. formates, acetates, oxalates, triflates, 2-ethylhexanoates and also naphthenates, metal alkoxides and metal chelates, e.g. chelates of acetylacetone, ethylacetoacetate, dimethylglyoxime, salicylaldehyde, 8-hydroxyquinoline or o-phenan-throline, which are dissolved in a suitable solvent or converted by appropriate reactions into a metal compound which readily forms a homogeneous solution. The precursor liquid should preferably be a homogeneous solution, but emulsions are also possible in principle. If a multifluid nozzle having a plurality of inlets for liquid is used, the fuel and the respective metal oxide precursor can also be atomized separately. In the ideal case, the fuel consists of an organic solvent in which the metal oxide precursor or precursors is/are dissolved. As solvent/fuel, particular preference is given to alcohols, organic acids and aromatic and/or aliphatic hydrocarbons.

Particle formation can be regarded as starting with the liquid precursor/solvent or fuel mixture being atomized to form fine droplets by the multifluid nozzle. In the flame, these droplets are exposed to very high temperatures (1500-2500 K). This leads to vaporization and subsequent reaction of the precursor(s) and the solvent or fuel (combustion). The vaporization and liberation can be influenced by droplet explosions due to superheating of the droplets. Likewise, decomposition of the precursor(s) (gas or liquid phase) or sublimation prior to the reaction is possible. Subsequently, the first molecules and molecule clusters of the metal oxides are formed as a result of the reaction. Coagulation of these first subnanometer particles forms larger particles which are still liquid in this high-temperature region of the flame and therefore melt together homogeneously. The particles thereby undergo a growth process. After all exothermic reactions have proceeded to completion, the process environment cools down and fusion of the particles is suppressed. This leads to "freezing" of the particles whose composition and shape therefore no longer changes.

The chemical composition, the morphology, the particle size and size distribution and product properties of the $SiO_2$ mixed oxide particles formed can be controlled in a targeted manner as a function of the type and amount of the metal oxide precursor(s) used, the fuel/solvent, the type and amount of atomization gas and amount of liquid fed in. The particle size and thus the specific surface area can be varied by means of the amount and energy content of the liquid precursor/solvent or fuel mixture and the type and amount of dispersing gas (cf. L. Mädler, W. J. Stark, and S. E. Pratsinis, "Flame-made ceria nanoparticles," Journal of Materials Research, vol. 17, pp. 1356-1362, 2002; L. Mädler, H. K. Kammler, R. Mueller, and S. E. Pratsinis, "Controlled synthesis of nanostructured particles by flame spray pyrolysis", Journal of Aerosol Science, vol. 33, pp. 369-389, 2002). The phase structure (W. J. Stark, L. Mädler, M. Maciejewski, S. E. Pratsinis and A. Baiker, "Flame synthesis of nanocrystalline ceria-zirconia: effect of carrier liquid", Chemical Communications, pp. 588-589, 2003) and control over the morphology, i.e. the formation of hollow and/or compact particles (L. Mädler and S. E. Pratsinis, "Bismuth oxide nanoparticles by flame spray pyrolysis", Journal of the American Ceramic Society, vol. 85, pp. 1713-1718, 2002), can be influenced or effected, respectively, by means of the solvent.

The mixed oxides (a) preferably have, according to the invention, a mean primary particle size of from 3 to 100 nm, in particular from 5 to 40 nm, determined by measurement of the BET surface area.

The nanoparticulate mixed oxides of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu which have been prepared by flame spraying can be used as X-ray-opaque fillers.

The mixed oxides can be used as X-ray-opaque fillers in virtually any workpieces in which the presence of an X-ray-opaque filler is advantageous, e.g. for analytical purposes. They are preferably used in dental composites.

To produce the dental composites of the invention, the X-ray-opaque mixed oxide nanofillers prepared by flame spraying are dispersed in suitable polymerizable matrix resins, subsequently admixed with the photoinitiator system and, if appropriate, further additives and cured by thermal or light-induced polymerization. Furthermore, the filler content of a nanofilled composite can be increased further by incorporating the nanofillers into a prepolymerized filler.

As free-radically polymerizable matrix monomers, it is possible to use commercially available diluent monomers such as mono(meth)acrylates, e.g. Methyl, ethyl, butyl, benzyl, furfuryl or phenyl(meth)acrylate and also the polyfunctional acrylates or methacrylates known as crosslinker monomers, e.g. bisphenol A di(meth)acrylate, bis-GMA, UDMA, diethylene, triethylene or tetraethylene glycol di(meth)acrylate, 1,10-decanediol di(meth)acrylate, trimethyolpropane tri(meth)acrylate, pentaerthyritol tetra(meth)acrylate and also butanediol di(meth)acrylate or 1,12-dodecanediol di(meth)acrylate. As free-radically polymerizable oligomers or polymers bearing terminal and/or lateral free-radically polymerizable groups, it is possible to use, for example, free-radically polymerizable α,ω-(meth)acryoyl-terminated polyester, polyether, polyepoxide-amine or polyurethane telechelics or polycondensates of silicic acid which can be obtained, for example, by hydrolycic condensation of silanes bearing free-radically polymerizable groups, preferably methacrylic or acrylic groups. Such polycondensates of silicic acid are also described in DE 44 16 857 C1 or DE 41 33 494 C2.

Possible matrix monomers for cationic photopolymers are, in particular, cationically polymerizable diluent or crosslinker monomers such as glycidyl ethers or cycloaliphatic epoxides, cyclic ketene acetals, vinyl ethers, spiroorthocarbonates, oxetanes or bicyclic ortho esters. Examples are: triethylene glycol divinyl ether, cyclohexanedimethanol divinyl ether, 2-methylene-1,4,6-trioxaspiro[2,2]nonane, 3,9-dimethylene-1,5,7,11-tetraoxaspiro[5,5]undecane, 2-methylene-1,3-dioxepane, 2-phenyl-4-methylene-1,3-dioxolane, bisphenol A diglycidyl ether, 3,4-epoxycyclohexylmethyl 3,4-epoxycyclohexanecarboxylate, bis(3,4-epoxycyclo-hexylmethyl) adipate, vinylcyclohexene dioxide, 3-ethyl-(3-hydroxymethyl)oxetane, 1,10-decanediylbis-(oxymethylene)bis(3-ethyloxetane) or 3,3-(4-xylylene-dioxy)bis(methyl-3-ethyloxetane). Further suitable cationically polymerizable matrix systems are poly-condensates of silicic acid which can be obtained, for example, by hydrolytic condensation of silanes bearing cationically polymerizable groups, preferably epoxide, oxetane, spiro ortho ester or vinyl ether groups. Such polycondensates of silicic acid are described, for example, in DE 41 33 494 C2 or U.S. Pat. No. 6,096,903.

To initiate the free-radical polymerization, polymerization initiators, preferably thermal initiators and/or photoinitiators, are added to the compositions used according to the invention. Preferred examples of thermal initiators are the known peroxides, e.g. dibenzoyl peroxide, dilauryl peroxide, tert-butyl peroctoate or tert-butyl perbenzoate, and also diethyl azobisisobutyrate or azobisisobutyronitrile (AIBN), benzopinacol or 2,2-dimethylbenzopinacol. Examples of suitable photoinitiators are benzophenone, benzoin and derivatives thereof or α-diketones or derivatives thereof, e.g. 9,10-phenanthroquinone, 1-phenyl-1,2-propanedione, diacetylbenzil or 4,4-dichlorobenzil. Particular preference is given to using camphorquinone and 2,2-methoxy-2-phenylacetophenone and especially α-diketones in combination with amines as reducing agents, e.g. N-cyanoethyl-N-methylaniline, 4-(N,N-dimethylamino)benzoic esters, N,N-dimethylaminoethyl methacrylate, N,N-dimethyl-sym-xylidene or triethanol-amine. Furthermore, acylphosphines such as 2,4,6-tri-methylbenzoyldiphenylphosphine oxide or bis(2,6-dichlorobenzoyl)-4-N-propylphenylphosphine oxide are also particularly suitable. Dual curing of free-radically and cationically polymerizable systems can be carried out using, in particular, diaryliodonium or triarylsulfonium salts, e.g. triphenylsulfonium hexafluorophosphate or hexafluoroantimonate.

As initiators for a polymerization carried out at room temperature, use is made of redox initiator combinations, e.g. combinations of benzoyl peroxide or lauryl peroxide with N,N-dimethyl-sym-xylidene or N,N-dimethyl-p-toluidine.

To achieve an optimum bond between matrix and filler particles, the latter are usually surface-treated with silanes containing suitable groups capable of polymerization, e.g. (meth)acrylic, vinyl, oxetane or epoxide groups.

To improve the mechanical properties, the compositions used according to the invention can also be filled with further organic or inorganic particles or fibers. Preferred inorganic particulate fillers are nanoparticulate or microfine fillers, e.g. pyrogenic silica or precipitated silica, or macrofillers or minifillers, e.g. quartz, glass-ceramic or glass powders having an average particle size of from 0.01 to 5 μm, or X-ray-opaque fillers such as ytterbium trifluoride. Furthermore, it is also possible to use titanium fibers, glass fibers, polyamide fibers or carbon fibers. Finally, the compositions used according to the invention can contain further additives such as stabilizers, flavors, microbiocidal ingredients, optical brighteners, plasticizers or UV absorbers.

A preferred composition for use according to the invention comprises:

(a) from 5 to 90% by weight, in particular from 10 to 70% by weight, of at least one nanoparticulate mixed oxide (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu, where the mixed oxides have been prepared by flame spraying, and (b) from 0 to 80% by weight, in particular from 0 to 50% by weight, based on the composition, of at least one matrix monomer, (c) from 0.1 to 5% by weight, in particular from 0.2 to 2.0% by weight, based on the composition, of polymerization initiator, and/or (d) from 0 to 90% by weight, in particular from 0 to 80% by weight, based on the composition, of further fillers, (e) from 0.0001 to 0.5% by weight, in particular from 0.001 to 0.3% by weight, based on the composition, of colorants, (f) from 0.001 to 2.0% by weight, in particular from 0.1 to 1.0% by weight, based on the composition, of further additives, where the proportions of the components (a) to (f) add up to 100% by weight.

A particularly preferred composition to be used according to the invention comprises:

(a) from 5 to 90% by weight, in particular from 10 to 70% by weight, of at least one nanoparticulate mixed oxide (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu, where the mixed oxides have been prepared by flame spraying, and (b) from 0 to 80% by weight, in particular from 0 to 50% by weight, based on the composition, of at least one matrix monomer, (c) from 0.1 to 5% by weight, in particular from 0.2 to 2.0% by weight, based on the composition, of polymerization initiator, and/or (d) from 0 to 90% by weight, in particular from 0 to 80% by weight, based on the composition, of further fillers, where the proportions of the components (a) to (d) add up to 100% by weight.

In a further embodiment, the dental composites of the present invention are free of apatites.

The dental composites of the invention can be used, for example, in a method for filling, surface sealing or restoring teeth by introducing them directly into dental cavities or applying them to the surfaces of teeth. Additionally, the dental composites of the invention can be used for purposes of preparing dental prostheses, dental bridges, and/or tooth replacement pieces. The dental composites can also be used as adhesives, cements and/or facing material for dental applications.

In a further possible use for the production of inlays or onlays, a mold can be made of a tooth cavity and then used to manufacture a matching inlay or onlay. Furthermore, the composites of the invention can be used for filling or coating any substrates, in particular teeth.

In the normal way of using the composites, they are successively (I) applied or introduced into a mold,
(II) if desired, shaped or molded,
(III) if desired, partially cured,
(IV) if desired, subjected to further shaping,
(V) cured and
(VI) if desired, subsequently subjected to further processing.

The invention is illustrated below with the aid of the figures and with the aid of examples.

FIG. 1 shows (scale in nm) transmission electron micrographs (TEM) of differing magnification (at left 10 000×; at right 50 000×) of a $Yb_2O_3/SiO_2$ mixed oxide powder (30% by mass of $Yb_2O_3$) prepared by flame spraying. The overview micrographs show the morphological homogeneity of the product which is made up of partly aggregated primary particles. The primary particles of the powder have a spherical shape.

Figure 2:
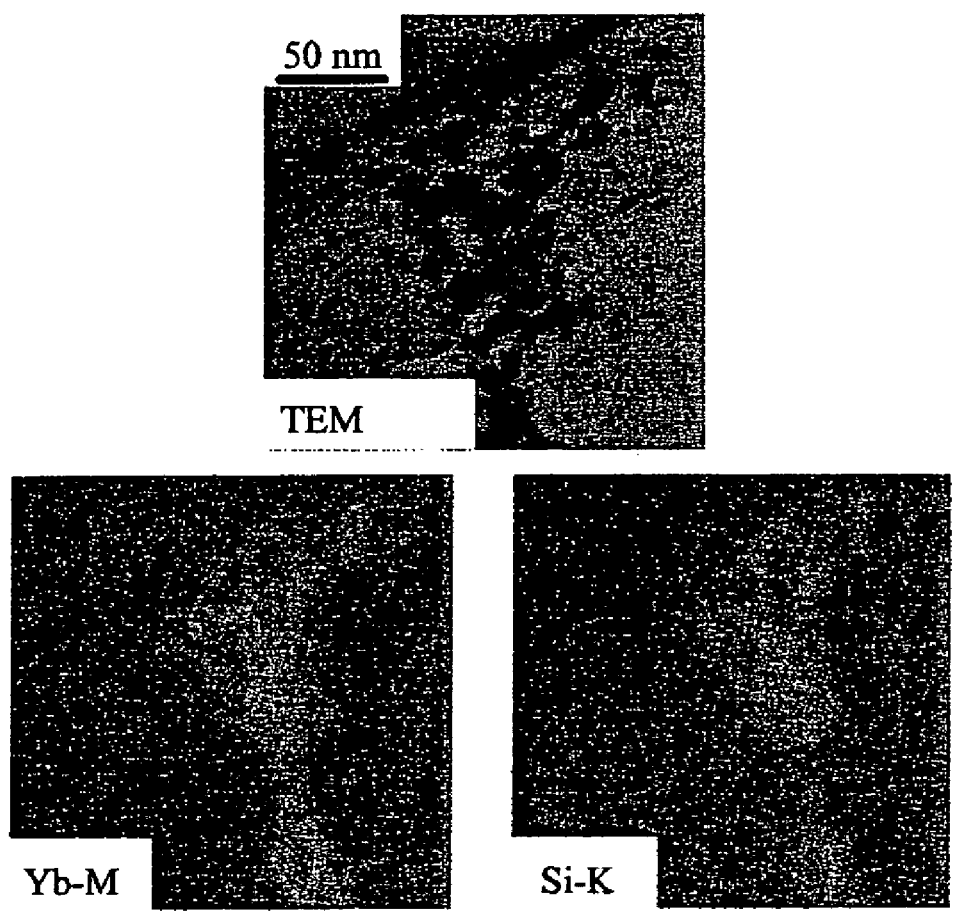

FIG. 2 shows an electron micrograph of a Yb/Si mixed oxide (50% by mass of $Yb_2O_3$) prepared by flame spraying (uppermost picture). At this $Yb_2O_3$ content too, the primary particles are spherical. The lower pictures show the electron spectroscopic images (ESI) for the energy absorption edges of Yb-M (1.53 and 1.58 keV) (middle) and Si—K (1.84 keV) (bottommost picture). Comparison of the two lower pictures clearly shows that the Yb and Si atoms are distributed very homogeneously. This homogeneous distribution is also given within the individual particles even at very short length scales.

Figure 3:
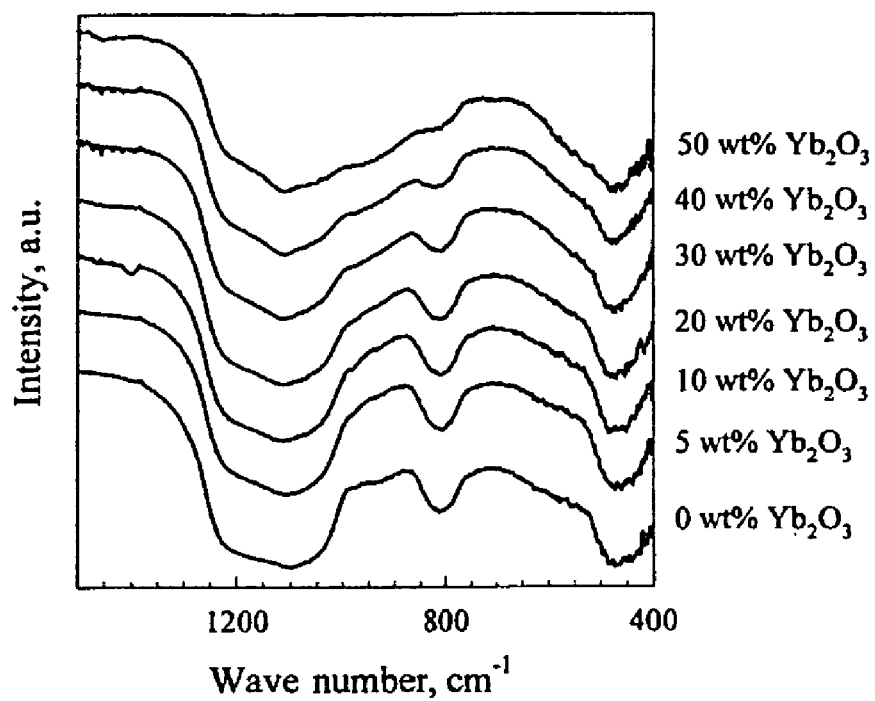

FIG. 3 shows DRIFTS spectra (diffuse reflection infrared Fourier transform spectroscopy) of Yb/Si mixed oxides having differing $Yb_2O_3$ contents (from 0 to 50% by mass) which have been prepared by flame spraying.

Addition of ytterbium results in a broad absorption signal in the range from 1000 to 900 $cm^{-1}$ whose intensity increases with increasing ytterbium content. This broad absorption band corresponds to degenerate vibration modes which are caused by the presence of ytterbium. The increase in the intensity of the absorption with increasing ytterbium content is evidence for the atomic distribution of the ytterbium in the powder.

Figure 4:
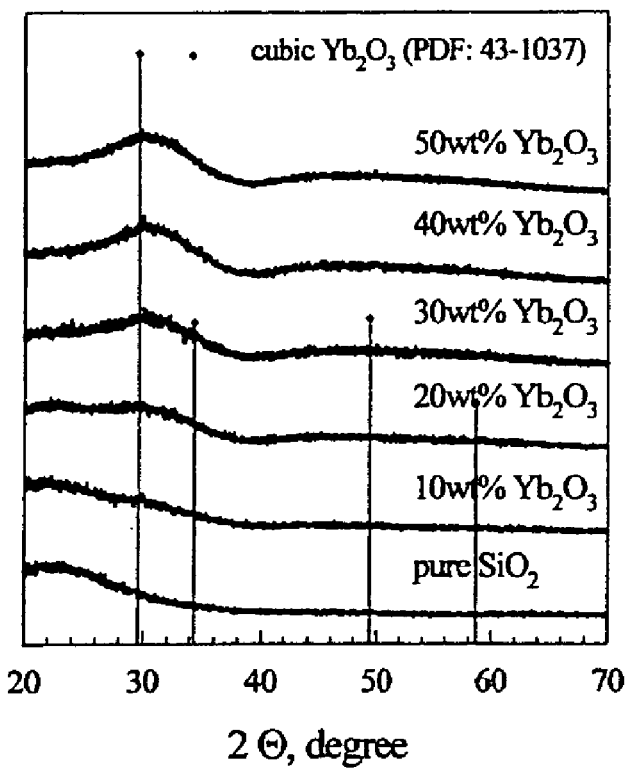

FIG. 4 shows XRD (X-ray diffraction) patterns of Yb/Si mixed oxides having differing $Yb_2O_3$ contents (from 0 to 50% by mass) which have been prepared by flame spraying. The diffraction pattern of pure cubic $Yb_2O_3$ is indicated by vertical lines. None of the powders displays a pronounced X-ray diffraction pattern; accordingly, all samples are X-ray-amorphous. Neither $Yb_2O_3$ crystals nor ytterbium silicates were able to be detected.

EXAMPLES

The measurement data reported in the examples were obtained in accordance with EN ISO 4049 (2000) "Dentistry—polymers for fillings, restorative work and fixing":

Flexural Strength and Flexural Modulus:

Test specimens having dimensions of 25 mm*2 mm*2 mm are produced from the composite paste in appropriate steel molds and cured using a dental radiation source Spectramat (Ivoclar Vivadent) for 3 minutes per side, i.e. 2*3 minutes. After the test specimens had been stored in water at 37° C. for 24 hours, the mechanical properties were determined using a universal tester Z010 from Zwick.

Transparency:

In a ChromaMeter CT-310 (Minolta), a beam of white light is, for the purposes of calibration, passed through a cell (path length: 2 mm) filled with water, which corresponds to a transparency of 100%. The cell is then replaced by a composite test specimen (path length: 1 mm) and the transmitted light is measured in comparison with the water-filled cell, which then corresponds to the transparency of the composite.

X-ray Opacity:

X-ray photographs of a composite test specimen having a thickness of 2 mm and a stepped Al calibration standard having steps of 0.5 mm are taken together by means of a dental X-ray camera and the blackness of the composite specimen and the stepped Al calibration standard are compared. The blackness of 2 mm of Al corresponds to an X-ray opacity of 100% Al.

Example 1

Synthesis of Mixed Oxides of the Elements Si and Yb

A two-fluid nozzle was used at a liquid inflow rate of 5 ml/min. The atomization gas was oxygen (5 l/min). The support flame was operated using premixed methane/oxygen (1.5 l/min/3.2 l/min). The enveloping air stream was 5 l/min of oxygen. The precursors used for Si and Yb were tetraethoxysilane (TEOS) and ytterbium nitrate pentahydrate ($Yb(NO)_3.5H_2O$), respectively. To remove all water of crystallization from the Yb precursor, $Yb(NO)_3.5H_2O$ was reacted in 18.75% by volume of acetic anhydride and 81.25% by volume of 2-ethylhexanoic acid at 107° C. under inert gas ($N_2$). In this reaction, all oxides of nitrogen were driven off and the water was removed by reaction with acetic anhydride to form acetic acid. The solution formed in this way was mixed with 45.08% by volume of xylene and TEOS to give a total metal concentration of 0.5 mol/l. Various Yb/(Yb+Si) ratios could easily be set using this method. Solutions containing up to 50% by mass of $Yb_2O_3$, based on the nominal total oxide weight, could be prepared in this way. For solutions having a nominal ytterbium oxide content of significantly below 50% by mass, the solution was diluted with a mixture of acetic anhydride and 2-ethyl-hexanoic acid (about 3:13 by volume). This made it possible to alter the Yb concentration without changing the total enthalpy of the solution. The powder prepared had spherical primary particles (cf. FIG. 1).

Furthermore, a homogeneous atomic distribution of Si and Yb atoms in the mixed oxide was achieved (cf. FIG. 2). This was able to be confirmed by means of infrared spectroscopy (cf. FIG. 3). All powders prepared were X-ray-amorphous, as could be confirmed by XRD measurements (cf. FIG. 4). The index of refraction of the mixed oxide powders could be set very precisely by means of the ytterbium content. Table 1 shows examples for from 10 to 50% by mass of $Yb_2O_3$ with indices of refraction of from 1.449 to 1.560. It was able to be shown that these powders obeyed Appen's law, i.e. a linear increase with atom fraction of Yb (Table 1).

TABLE 1

Experimentally determined indices of refraction of $Yb/SiO_2$ mixed oxides

| $Yb_2O_3$ (% by mass) | $Yb_2O_3$ (mol %) | Index of refraction |
|---|---|---|
| 10 | 3.3 | 1.499 |
| 20 | 7.1 | 1.513 |
| 30 | 11.5 | 1.523 |
| 40 | 16.9 | 1.539 |
| 50 | 23.3 | 1.560 |

Table 2 shows by way of example how the specific surface area of the powder can be altered significantly or set by means of the flame characteristics, in the present case changes in the amount of atomization air (reduction from 5 l/min to 3 l/min) and the feed rate of liquid (increase from 5 ml/min to 8 ml/min). These changes had virtually no influence on the index of refraction of the powder.

TABLE 2

Alteration of the specific surface area of the Yb/Si mixed oxide powders by variation of the flame spraying parameters

| Atomization gas (l/min) | Flow rate of liquid (ml/min) | Specific surface area ($m^2/g$) | Index of refraction |
|---|---|---|---|
| 5 | 5 | 245 | 1.530 |
| 8 | 3 | 135 | 1.523 |

Example 2

Evaluation of the Thickening Action of the Mixed Oxides of the Elements Si and Yb Prepared as Described in Example 1

To examine the thickening action, model composite pastes were prepared from 16.5% of Yb/Si mixed oxide of differing specific surface areas and 83.5% of a free-radically polymerizable monomer composition (41.82 parts of bis-GMA, 37 parts of UDMA, 20 parts of TEGDMA, 0.73 part of photoinitiator, 0.55 part of additives). 0.1 g of paste was loaded between two glass plates under a load of 120 g for a period of three minutes and the resulting diameter of the paste was determined. The thinner this "disc consitency" of the paste, i.e. the lower the thickening action, the greater the diameter obtained. The results demonstrate that the consistency of the pastes depends significantly on the specific surface area of the nanoparticle filler (Table 3).

TABLE 3

Influence of the specific surface area of the mixed oxide filler on the disc consistency of the composite pastes

| Specific surface area ($m^2/g$) | Disc consistency (mm) |
|---|---|
| 399 | 11.7 |
| 365 | 18.5 |
| 291 | 24.4 |
| 233 | 33.3 |
| 205 | 36.0 |
| 125 | 38.1 |

The thickening action can be reduced by agglomerate formation. Agglomeration is effected, for example, by placing 37.5% of deionized water in a vessel and slowly stirring 62.4% of mixed oxide and 0.16% of potassium fluorozirconate into it until a homogeneous suspension is obtained. This suspension is dried at 120° C. for 30 hours, milled in a ball mill and sieved. The agglomerated filler obtained in this way can then be used for producing a composite.

Example 3

Production of a Filling Composite Based on a Mixed Oxide of the Elements Si and Yb Prepared as Described in Example 1

A composite (composite A) was produced from 48% by mass of a light-curing monomer composition (41.82 parts of bis-GMA, 37 parts of UDMA, 20 parts of TEGDMA, 0.73 part of photoinitiator, 0.55 part) and 52% by mass of an X-ray-opaque Yb/Si mixed oxide having a $Yb_2O_3$ content of 30% by mass and a specific surface area of 125 $m^2/g$ which had been prepared by flame spraying as described in Example 1. As a comparative example, a composite (composite B) was produced from 50% by mass of the same light-curing monomer, 35% by mass of silanized pyrogenic $SiO_2$ OX-50 and 15% by mass of ytterbium fluoride, and the transparency and X-ray opacity were determined after curing of the composites:

TABLE 4

Transparency and X-ray opacity of the composites from Example 3

| Material | Transparency (%) | X-ray opacity (% Al) |
|---|---|---|
| Composite A | 13.2 | 180 |
| Composite B | 9.5 | 150 |

The results show that an acceptable transparency and X-ray opacity were achieved using the X-ray-opaque Yb/Si mixed oxide. To obtain a composite having a comparable X-ray opacity using conventional nanofillers such as OX-50, the addition of over 15% of ytterbium fluoride is necessary. However, two fillers having different indices of refraction are then present, which has an adverse effect on the transparency.

Example 4

Production of a Filling Composite Based on a Prepolymerized Filler Prepared from a Mixed Oxide Prepared as Described in Example 1

A prepolymerized filler (prepolymer) was prepared first. For this purpose, a homogeneous mixture was prepared from 70 g of X-ray-opaque Yb/Si mixed oxide (30% by mass of $Yb_2O_3$ and specific surface area of 125 m$^2$/g) prepared by flame spraying as described in Example 1 and 30 g of a heat-curing monomer composition (80% of decanediol dimethacrylate, 12% of UDMA, 8% of dibenzoyl peroxide) and this was then polymerized at 120° C. for 1 hour and milled to a particle size of 10-20 µm. Finally, a composite paste was produced from this prepolymer (44% by mass, 24% by mass of a light-curing monomer composition (41.82 parts of bis-GMA, 37 parts of UDMA, 20 parts of TEGDMA, 0.73 part of photoinitiator, 0.55 part of additives) and a further 33% by mass of X-ray-opaque Yb/Si mixed oxide (30% by mass of $Yb_2O_3$ and specific surface area of 125 m$^2$/g) prepared by flame spraying as described in Example 1. Test specimens were then prepared from this, cured in a Spectramat (Ivoclar Vivadent) light oven for 2×3 minutes and stored in water at 37° C. for 24 hours. The following properties were then determined:

| | |
|---|---|
| Flexural strength | 110 MPa |
| Flexural modulus of elasticity | 6500 MPa |
| Transparency | 14% |
| X-ray opacity | 300% Al |

Example 5

Production of a Filling Composite Based on a Yb/Si Mixed Oxide and a Conventional Glass Filler A composite was produced from 20% by mass of a light-curing monomer composition (41.82 parts of bis-GMA, 37 parts of UDMA, 20 parts of TEGDMA, 0.73 part of photoinitiator, 0.55 part of additives), 40% by mass of an X-ray-opaque Yb/Si mixed oxide (30% by mass of $Yb_2O_3$ and specific surface area of 125 m$^2$/g) prepared by flame spraying as described in Example 1 and 40% by mass of a silanized Ba—Al silicate glass (GM 27884 from Schott) having a mean particle size of 1.0 µm. Test specimens were prepared from this, cured in a Spectramat (Ivoclar Vivadent) light oven for 2×3 minutes and stored in water at 37° C. for 24 hours. The following properties were then determined:

| | |
|---|---|
| Flexural strength | 130 MPa |
| Flexural modulus of elasticity | 9000 MPa |
| Transparency | 14% |
| X-ray opacity | 400% Al |

These results demonstrate that the X-ray-opaque $Yb_2O_3$/$SiO_2$ nanofiller having an index of refraction of 1.53 can be combined, for example, with Ba—Al silicate glasses without a deterioration in the transparency being observed. In contrast, combining $SiO_2$ nanofillers of the prior art with X-ray-opaque glasses usually leads to a deterioration in the transparency, since the indices of refraction of the two fillers are far apart and do not coincide.

The invention claimed is:

1. A dental composite comprising at least one nanoparticulate mixed oxide (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu which has been prepared by flame spraying and wherein the mixed oxides have at least one of the following features:
   a) an amorphous structure,
   b) a homogeneous element distribution,
   c) a very low organic content,
   d) an X-ray opacity which can be varied,
   e) an index of refraction which can be varied, and
   f) a shperical particle shape.

2. A dental composite as claimed in claim 1, wherein the mixed oxides (a) are mixed oxides of $SiO_2$ with an X-ray-opaque metal oxide of Yb, in particular $SiO_2/Yb_2O_3$.

3. A dental composite as claimed in claim 1, comprising one mixed oxide (a).

4. A dental composite as claimed in claim 1, wherein (a) from 5 to 90% by weight, based on the composition, of mixed oxides are present.

5. A dental composite as claimed in claim 1 which has an X-ray opacity of from 50 to 800% Al, and in which the mixed oxides (a) have a mean primary particle size of from 3 to 100 nm, determined by measurement of the BET surface area, have an index of refraction of from 1.46 to 1.70, and/or have an organic content of less than 0.5% by mass, of oxidizable carbon.

6. A process for producing dental composites which comprises
   (i) preparing nanoparticulate mixed oxides (a) of $SiO_2$ with X-ray-opaque metal oxides of one or more elements selected from the group consisting of Y, La, Ta, Ce, Pr, Nd, Sm, Eu, Gd, Tb, Dy, Ho, Er, Tm, Yb, Lu by flame spraying,
   (ii) dispersing the mixed oxides (a) in suitable polymerizable matrix resins,
   (iii) adding a polymerization initiator (c),
   (iv) if desired, mixing the dispersion with further constituents matrix monomer (b), further fillers (d), colorants (e) and/or further additives (f) and
   (v) subsequently curing the dispersion by thermal or light-induced polymerization.

7. A method for filling, surface sealing or restoring teeth, said method comprising applying the dental composite as claimed in claim 1 to teeth.

8. A dental prosthesis, dental bridge or similar tooth replacement piece comprising a dental composite as claimed in claim 1.

9. A method for filling, surface sealing or restoring teeth, wherein the dental composite as claimed in claim 1 is introduced into a mold, and cured and applied to teeth.

10. An adhesive, cement and/or facing material cement for dental applications comprising the composite as claimed in claim 1.

11. A dental composite prepared by the process of claim 6.

12. A method for filling, surface sealing or restoring teeth comprising applying the dental composite prepared by the process of claim 6 to teeth.

13. A dental prosthesis, dental bridge and/or similar tooth replacement piece comprising a dental composite prepared by the process of claim 6.

14. A method for filling, surface sealing or restoring teeth, wherein the dental composites prepared by the process of claim 6 are introduced into a mold and cured and applied to teeth.

15. An adhesive, cement and/or facing material cement for dental applications comprising the dental composite prepared by the process of claim 6.

16. A dental composite comprising:

nanoparticulate mixed oxides (a) of $SiO_2$ with X-ray-opaque metal oxides of one or more elements selected from the group consisting of: Y, La, Ta, Ce, Pr, Nd, Sm, Eu, Gd, Tb, Dy, Ho, Er, Tm, Yb, Lu, prepared by flame spraying, suitable polymerizable matrix resins, polymerization initiator (c), and optionally, further constituents matrix monitor (b), further fillers (d), colorants (e) and/or further additives (f).

17. A dental composite as claimed in claim 1, wherein the mixed oxides (a) are $SiO_2/YbO_3$ mixed oxides.

* * * * *